United States Patent [19]

Sakagami

[11] Patent Number: 5,264,182
[45] Date of Patent: Nov. 23, 1993

[54] SAMPLLE AND REAGENT DELIVERY DEVICE WITH A PROBE AND PROBE SUPPORTING MEMBER FOR PREVENTING CONTAMINATION

[75] Inventor: Toshio Sakagami, Chofu, Japan

[73] Assignee: Olympus Optical Co, Ltd., Tokyo, Japan

[21] Appl. No.: 38,354

[22] Filed: Mar. 22, 1993

Related U.S. Application Data

[62] Division of Ser. No. 506,077, Apr. 9, 1990, Pat. No. 5,213,761.

[30] Foreign Application Priority Data

Apr. 12, 1989 [JP] Japan ................................. 1-90543
Apr. 12, 1989 [JP] Japan ................................. 1-90544

[51] Int. Cl.$^5$ ........................................... G01N 35/04
[52] U.S. Cl. .......................................... 422/63; 422/64; 422/81; 422/99; 422/100; 73/863.82; 73/863.83; 73/864.21; 73/864.22; 435/291
[58] Field of Search ................... 422/63, 64, 65, 68.1, 422/81, 99, 100; 73/863.82, 863.83, 864.21, 864.22, 864.81; 435/288, 291

[56] References Cited

U.S. PATENT DOCUMENTS

| | | | |
|---|---|---|---|
| 3,951,608 | 4/1976 | Trod | 422/64 |
| 4,210,724 | 7/1980 | Sogi et al. | 422/64 |
| 4,340,390 | 7/1982 | Collins et al. | 422/64 |
| 4,774,055 | 9/1988 | Wakatake et al. | 422/64 |
| 4,785,677 | 11/1988 | Higo | 422/100 |
| 4,906,433 | 3/1990 | Minekane | 422/64 |
| 4,927,765 | 5/1990 | Saxon et al. | 436/49 X |
| 5,164,318 | 11/1992 | Sato et al. | 435/288 |

FOREIGN PATENT DOCUMENTS

55-140156 11/1980 Japan.

*Primary Examiner*—James C. Housel
*Assistant Examiner*—David Redding
*Attorney, Agent, or Firm*—Stevens, Davis, Miller & Mosher

[57] ABSTRACT

Dispensing apparatus for an automatic chemical analyzer including a reaction turntable having a plurality of reaction vessels arranged along a periphery thereof, a sample turntable having a plurality of sample vessels arranged along the periphery thereof, a reagent turntable having a plurality of reagent bottles in which different kinds of reagents are contained, a sample delivery mechanism for delivering a given amount of a sample into a reaction vessel, and a reagent delivery mechanism for delivering a given amount of a reagent into the sample to form a test liquid in the reaction vessel. The reagent delivery mechanism has a nozzle which can be moved between a reagent sucking position above a reagent bottle and a reagent discharging position above a reaction vessel; a plurality of detachable probes which are arranged in respective reagent bottles in such a manner that the tip of the nozzle can be inserted into a probe in a reagent bottle at the reagent sucking position; a syringe connected to the nozzle for sucking a given amount of a reagent into the probe coupled with the nozzle; and a probe removing mechanism for removing the probe from the tip of the nozzle after the reagent has been discharged into the reaction vessel and the probe has been returned into the reagent bottle from which the probe was picked-up by the nozzle.

5 Claims, 5 Drawing Sheets

FIG_2
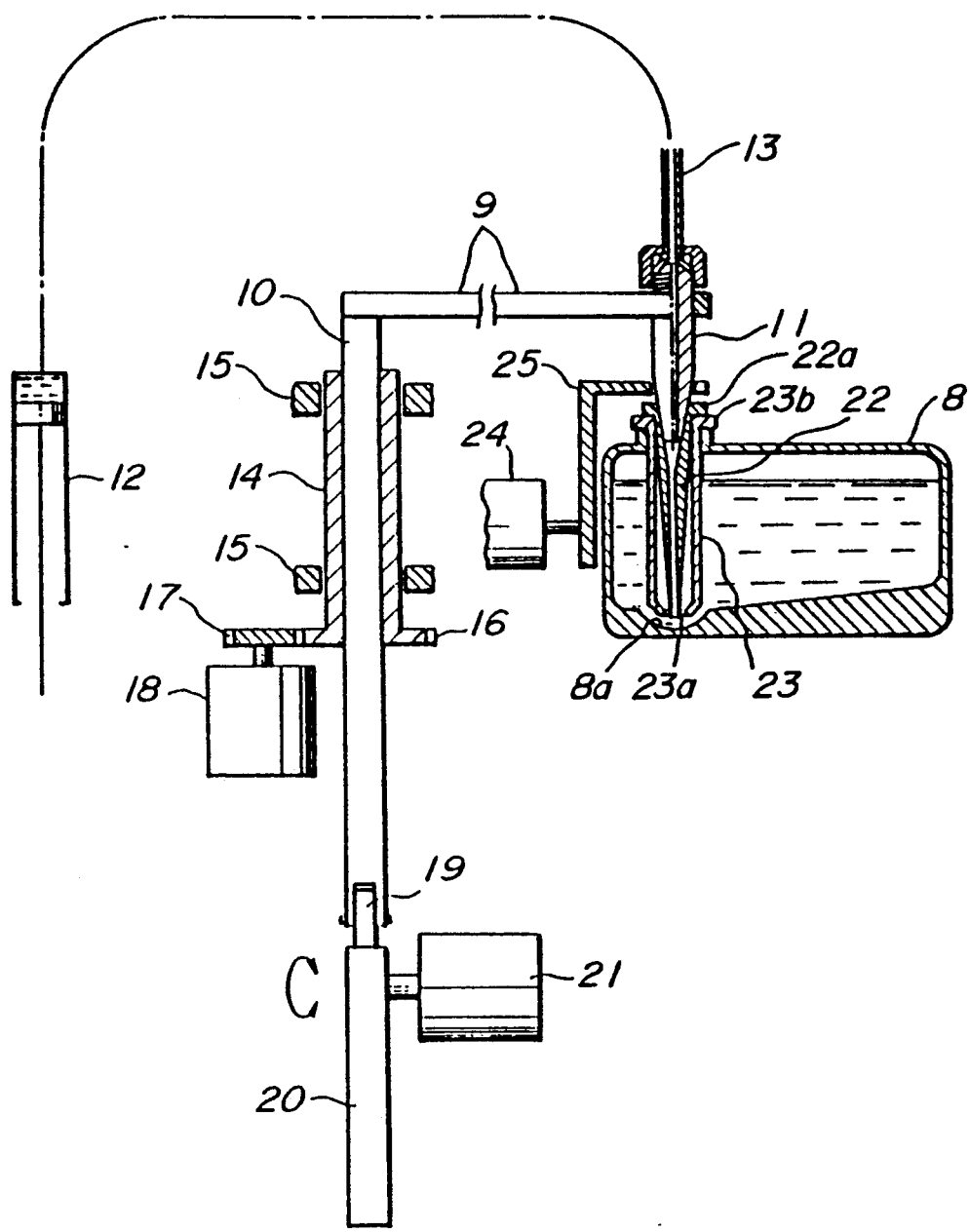

FIG_3
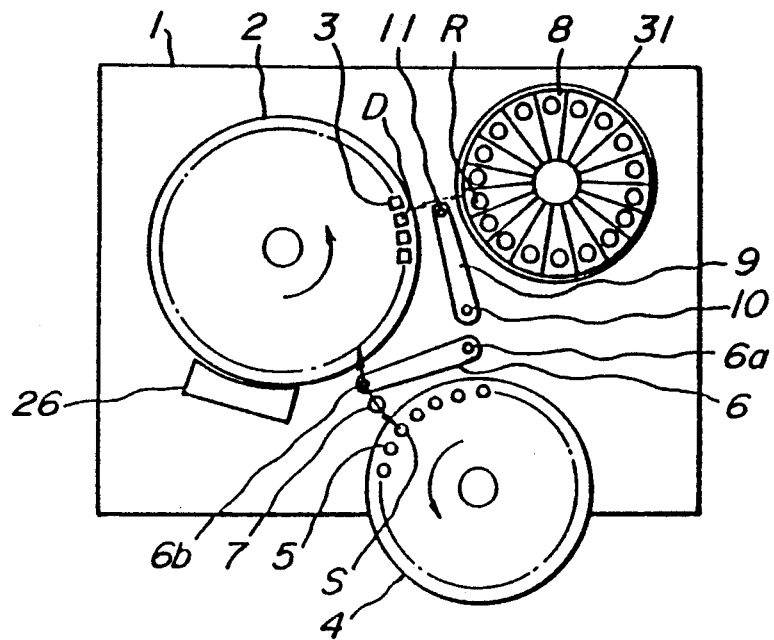
FIG_4
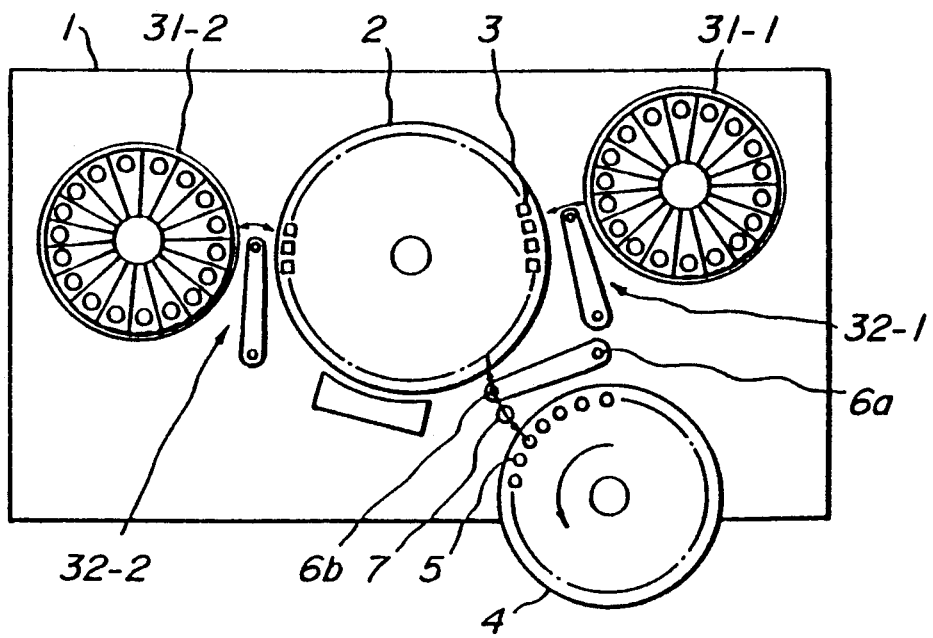

FIG_6
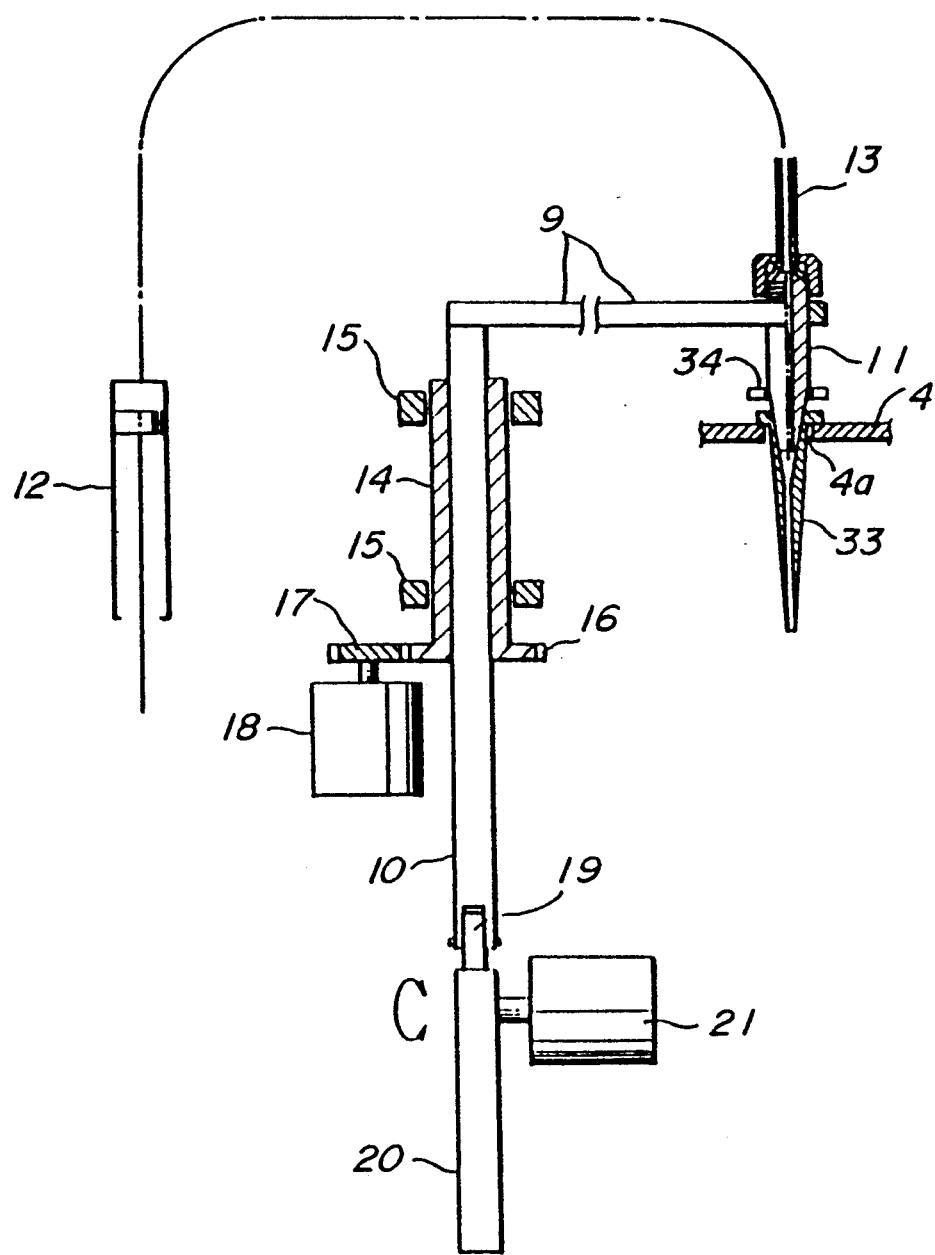

SAMPLLE AND REAGENT DELIVERY DEVICE WITH A PROBE AND PROBE SUPPORTING MEMBER FOR PREVENTING CONTAMINATION

This is a division of application Ser. No. 07/506,077, filed Apr. 9, 1990 now U.S. Pat. No. 5,213,761.

BACKGROUND OF THE INVENTION

1. Field of the Invention and Related Art Statement

The present invention relates to all automatic chemical analyzer, and more particularly to an automatic chemical analyzer comprising a reagent delivering means for delivering different kinds of reagents without contamination.

There has been proposed an automatic chemical analyzer which can measure a plurality of substances contained in samples. Such an analyzer is usually called a multi-item analyzer. In such a multi-item analyzer, it is required to deliver various kinds of reagents without contamination therebetween.

In Japanese Patent Application Laid-open Publication Kokai Sho 55-140156, there is described a known multi-item analyzer in which a delivery probe and a conduit connected thereto are washed by conducting water or a diluent in time intervals between successive delivering operations which might cause the contamination. In Japanese Patent Publication No. 59-20089, there is also disclosed a known multi-item analyzer in which after discharging a given amount of a reagent through a reagent probe, a given amount of a diluent is discharged from the same reagent probe to wash an inner wall of the reagent probe.

In the known multi-item analyzers explained above, the reagent probe is washed at time intervals between successive delivering operations. That is to say, the inner wall of the reagent probe is washed by discharging the water or diluent through the reagent probe and the outer wall of the probe is washed by immersing a tip of the probe into a washing water. It is apparent that such a washing operation is time-consuming, so that the analyzing speed is limited. Moreover, the washing operation requires a large amount of the washing water or diluent, and thus the running cost of the analyzer may be expensive. Particularly, a latex type reagent might be adhered to the reagent probe strongly, so that it is rather difficult to remove the reagent adhered to the reagent probe only by washing and the contamination could not be avoided effectively. Nowadays the measuring sensitivity of the analyzer has become very high, and therefore if even a very small amount of the reagent remains on the reagent probe, there might be produced a serious problem due to the contamination. Particularly, the influence of the contamination is manifest in the immunological analysis.

In order to wash the outer wall of the reagent probe effectively, it has been proposed to limit the amount of descending movement of the probe, so that every time a predetermined length of the probe tip is inserted into the reagent. However, this measure requires a much more complicated construction and the cost of the analyzer becomes high.

There has also been proposed a multi-item analyzer in which a probe is detachably secured to a tip of a reagent delivery nozzle and after a reagent has been delivered, the probe is removed from the tip of the reagent nozzle and a new probe is set to the tip of the reagent nozzle. In this known analyzer, the problem of contamination between different kinds of reagents can be avoided completely, because the reagent is sucked exclusively into the detachable probe. However, a large number of probes have to be arranged in such a manner that the reagent delivery nozzle can pick them up successively. Therefore, the analyzer may be complicated in construction, large in size and expensive in cost. Further the used probes are wasted, and thus the running cost of analysis becomes very high.

It should be noted that the above explained problem of contamination also occurs in a sample probe for delivering successive different samples into reaction vessels. That is to say, in almost all known analyzers, the samples are delivered with the aid of a single sample probe and the sample probe is washed at time intervals between the deliveries of different samples in order to avoid contamination between the samples.

SUMMARY OF THE INVENTION

The present invention has for its object to provide a novel and useful automatic chemical analyzer in which the problem of contamination between different kinds of liquids to be delivered into reaction vessels can be effectively removed without washing the liquid delivery probe, while the whole analyzer can be made simple in construction, small in size and cheap in cost.

It is another object of the invention to provide an automatic chemical analyzer in which the analysis can be performed efficiently at a low running cost.

According to the invention, an automatic chemical analyzer including a sample holding means for holding a plurality of sample vessels in which a plurality of samples to be analyzed are contained, a reaction vessel holding means for holding a plurality of reaction vessels along a reaction line? a sample delivery means for delivering the samples held in the sample vessel holding means into the reaction vessels on the reaction line, a reagent holding means for holding a plurality of reagent bottles which contain a plurality of different kinds of reagents, a reagent delivery means for delivering the reagents into the reaction vessels on the reaction line, and a measuring means for measuring substances contained in a reaction liquid which is a mixture of a sample and at least one reagent and is contained in a reaction vessel is disclosed, the improvement therein being that said reagent delivery means comprises a delivery nozzle, a pump means connected to said delivery nozzle for sucking and discharging reagents, a plurality of detachable probes which are constructed to be detachably coupled with a tip of said delivery nozzle, a plurality of probe holding members each of which is arranged in respective one of said reagent bottles, a nozzle moving means for moving the delivery nozzle between a first position at which the tip of delivery nozzle can be coupled with a probe held in a probe holding member contained in a reaction bottle which contains a reagent to be delivered into a reaction vessel and a given amount of the reagent is sucked into the probe by operating said pump means, and a second position at which the probe is situated above the reaction vessel and the sucked reagent is discharged into the reaction vessel by operating said pump means, and a probe removing means for removing the probe from the tip of delivery nozzle into the probe holding member from which the probe has been taken out.

According to a further aspect of the invention, an automatic chemical analyzer including a sample holding means for holding a plurality of sample vessels in which a plurality of samples to be analyzed are contained, a reaction vessel holding means for holding a plurality of reaction vessels along a reaction line, a sample delivery means for delivering the samples held in the same vessels in the sample holding means into the reaction vessels on the reaction line, a reagent holding means for holding a plurality of reagent bottles which contain a plurality of different kinds of reagents, a reagent delivery means for delivering the reagents into the reaction vessels on the reaction line, and a measuring means for measuring substances contained in a reaction liquid which is a mixture of a sample and at least one reagent and is contained in a reaction vessel is disclosed, the improvement therein being that said sample delivery means and reagent delivery means comprise a common delivery nozzle;

a common pump means connected to said delivery nozzle for sucking samples and reagents;

a plurality of detachable sample delivery probes which are constructed to be detachably coupled with a tip of said delivery nozzle;

a plurality of detachable reagent delivery probes which are constructed to be detachably coupled with the tip of said delivery nozzle;

a plurality of sample probe holding members each of which is arranged in relation to one of said sample vessels;

a plurality of reagent probe holding members each of which is arranged in respective one of said reagent bottles;

a nozzle moving means for moving the delivery nozzle among a first position at which the tip of delivery nozzle can be coupled with a sample probe held in a sample probe holding member provided in relation to a sample vessel which contains a sample to be delivered into a reaction vessel, a second position at which the sample probe is immersed into the sample contained in said sample vessel and a given amount of the sample is sucked into the sample probe by operating said pump means, a third position at which the tip of delivery nozzle can be coupled with a reagent probe held in a reagent probe holding member contained in a reagent bottle which contains a reagent to be delivered into the reaction vessel and a given amount of the reagent is sucked into the reagent probe, and a fourth position at which sample and reagent probes are situated above the reaction vessel and the sucked sample and reagent are discharged into the reaction vessel;

a sample probe removing means for removing the sample probe from the tip of delivery nozzle into the sample probe holding member from which the sample probe has been taken out; and a reagent probe removing means for removing the reagent probe from the tip of delivery nozzle into the reagent probe holding member from which the reagent probe has been taken out.

BRIEF DESCRIPTION OF THE DRAWINGS

FIG. 2 is a cross sectional view illustrating the reagent probe picking-up and removing mechanism in the analyzer shown in FIG. 1;

FIG. 3 is a schematic plan view depicting a second embodiment of the analyzer according to the invention;

FIG. 4 is a schematic plan view depicting a third embodiment of the analyzer according to the invention;

FIG. 6 is a cross sectional view illustrating the sample probe picking-up and removing mechanism of the analyzer shown in FIG. 5.

DESCRIPTION OF THE PREFERRED EMBODIMENTS

Figure 1:
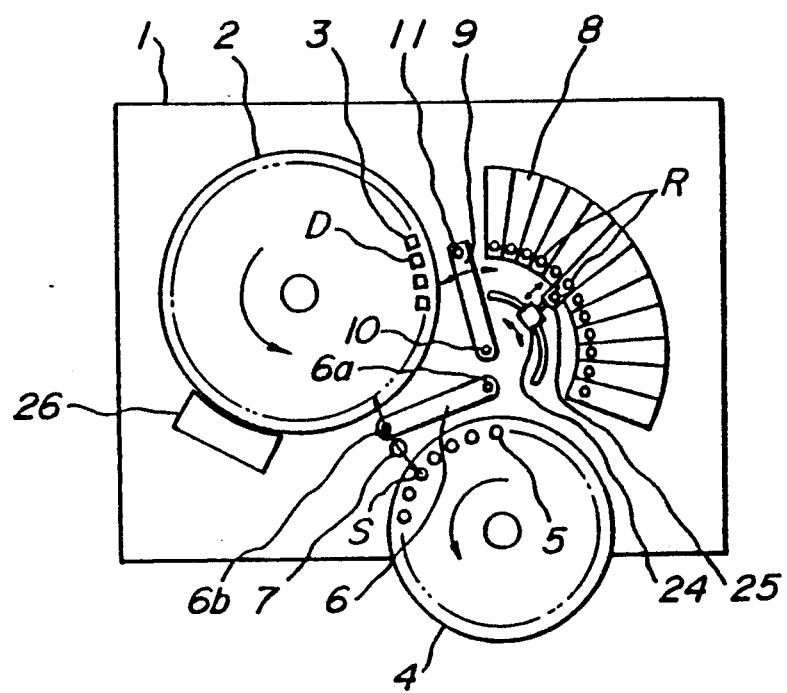
FIG. 1 is a schematic plan view showing a first embodiment of the automatic chemical analyzer according to the invention.

FIG. 1 is a schematic plan view showing a first embodiment of the automatic chemical analyzer according to the present invention. The analyzer comprises a base 1 and a reaction turntable 2 provided on the base rotatably in a direction shown by an arrow in a step-wise manner. On the reaction turntable 2 there are arranged a number of reaction vessels 3 along a periphery thereof at a constant pitch to form a circular reaction line. Each of the reaction vessels 3 is used to receive a mixture of a sample and a reagent and may be constructed by a disposable reaction vessel. It should be noted that the reaction vessels set on the reaction turntable 2 may be repeatedly used by effecting the washing. On the base 1 there is also arranged rotatably a sample turntable 4 and a large number of sample vessels 5 are arranged on the turntable equidistantly along the periphery thereof. In the sample vessels 5 are contained samples to be analyzed such as blood plasmas collected from different patients. The sample turntable 4 is rotated in the step-wise manner. Between the reaction turntable 2 and the sample turntable 4 there is arranged a sample delivery device. This device comprises an arm 6 which is swingably provided on the base 1 about a shaft 6a at one end and a sample delivery nozzle 6b secured to the other end of arm 6. As usual the sample delivery nozzle is coupled with a sample delivery syringe not shown in FIG. 1. The arm 6 is swung by driving mechanism in such manner that the sample delivery nozzle 6b is indexed into a sample sucking position S at which a tip of the sample delivery nozzle is inserted into a sample contained in a sample vessel 5 which is just indexed at the sample delivery position S, and into a liquid discharging position D above a reaction vessel 3 which is just indexed at the sample discharging position. In order to wash the sample delivery nozzle 6b, a washing vessel 7 is arranged between the reaction turntable 2 and the sample turntable 4. After a sample has been delivered from a sample vessel 5 into a reaction vessel 3, the tip of nozzle 6b is inserted into a washing vessel 7 to wash an outer wall of the nozzle and at the same time a washing liquid is discharged through the nozzle to wash an inner wall thereof.

On the base 1 there is further arranged a plurality of reagent bottles 8 each containing different kinds of reagents for measuring different kinds of substances contained in the samples. Between the reagent bottles 8 and the reaction turntable 2 is arranged a reagent delivery device. The reagent delivery device comprises an arm 9 which is swingably provided about a shaft 10 at one end, and a reagent nozzle 11 secured at the other end of the arm. As clearly shown in FIG. 2, the nozzle 11 is connected to a syringe 12 via a flexible tube 13. It should be noted that the nozzle 11 and tube 13 are filled with the liquid such as water and diluent. The shaft 10 is slidably supported by a first bearing 14 which is rotatably supported by a second bearing 15. In the lower end of the first bearing 14 is secured a gear 16 which is engaged with a driving gear 17 connected to a driving shaft of a first motor 18. On the lower end of the shaft 10 is rotatably arranged a roller 19 which serves as a cam follower and is urged against a peripheral surface of a disc-shaped cam 20, and the disc-shaped cam 20 is rotated by a second motor 21. When the first motor 18 is energized, the shaft 10 is rotated to index the nozzle 11 into the liquid discharging position D above the reaction vessel 3 and into a plurality of reagent sucking positions R above the reagent bottles 8. When the second motor 21 is energized to rotate the cam 20, the shaft 10 is moved up and down at a reagent sucking position R. In this manner, the nozzle 11 can be moved along a given locus. As clearly shown in FIG. 2, the tip of the nozzle 11 is inserted into a probe 22 which is arranged in a probe supporting member 23 provided in a reagent bottle 8. According to the invention, the probe 22 is detachably secured to the tip of nozzle 11. To this end, the tip of nozzle 11 is tapered and the upper mouth of probe 22 is widened upward. The probe 22 has a flange 22a formed at its upper end. A probe holding member 23 comprises a tube-like main body having an opening 23a formed in its bottom and a flange 23b formed at its top end. The reagent bottle 8 has an inclined inner bottom surface in which is formed a depression 8a. The probe 22 is formed to have such a length that a tip of the probe is slightly protruded into the depression 8a through the opening 23a of the probe holding member 23 under such a condition that the flange 22a of the probe 22 is placed on the flange 23b of the probe holding member 23 as illustrated in FIG. 2.

Now the operation of the analyzer of the first embodiment will be explained in detail. In the present embodiment, the sample delivery is carried out with the aid of the usual sample delivery mechanism so that its explanation is dispensed with. After a given amount of a sample contained in a sample vessel 5 provided on the sample turntable 4 is delivered into a reaction vessel 3 arranged on the reaction turntable 2, the first motor 18 is driven to rotate the arm 9 such that e nozzle 11 is indexed into a reagent sucking position R above a reagent bottle 8 which contains a given reagent to be delivered into the relevant reaction vessel 3. It should be noted that during the rotating movement of the arm 9, the shaft 10 is kept in the upper position. Then, the second motor 21 is energized to rotate the cam 20 to descend the shaft 10 until the tip of nozzle 11 is fully inserted into an upper mouth of a probe 22 held in a probe supporting member 23 contained in the relevant reagent bottle 8. In this manner, the probe 22 is connected to the syringe 12. Then, a plunger of the syringe 12 is pulled by a predetermined stroke to suck a given amount of the reagent into the probe 22. It should be noted that according to the invention the reagent is not sucked into the nozzle 11, but has to remain within the probe 22. As explained above the non-compressible liquid such as water and diluent is filled in the nozzle 11, tube 13 and syringe 12, so that the reagent can be sucked into the probe 22 accurately. In this case it is advantageous to provide a thin air layer between the non-compressible liquid and the sucked reagent so as to avoid the dilution of the reagent. After a given amount of the reagent has been sucked into the probe 22, the second motor 21 is energized to rotate the cam 20 and to ascend the arm 9, Since the tip of nozzle 11 is inserted firmly into the probe 22, the probe also ascends together with the nozzle 11. After the arm 9 has been lifted into the uppermost position, the first motor 18 is energized to rotate the arm 9 with the nozzle 11 and probe 22 into the reagent discharging position D above the relevant reaction vessel 3. Next the plunger of the syringe 12 is pushed to discharge the reagent held in the probe 22 into the reaction vessel 3. After that, the first motor 18 is energized again to rotate the arm 9 into a position above the relevant reagent bottle 8 from which the reagent had been sucked. Then the second motor 21 is energized to descend the arm 9 until the probe 22 fixed to the tip of nozzle 11 is inserted into the probe holding member 23 from which the relevant probe has been picked-up. Then a probe removing mechanism is driven to remove the probe 22 from the tip of nozzle 11. In the present embodiment, the probe removing mechanism comprises a solenoid 24 and a fork plate 25 connected to the solenoid. As illustrated in FIG. 1, the assembly of the solenoid 24 and fork plate 25 is arranged to move along a substantially semi-circular guide provided along the array of the reagent bottles 8. It should be noted that when the nozzle 11 having the probe 22 secured thereto is pulled out of and is inserted into the reagent bottle, the fork plate 25 is moved into a position at which the fork plate does not interact with the probe 22. After the probe 22 has been returned into the reagent bottle 8, the solenoid 24 is energized to protrude the fork plate 25 such that the nozzle 11 is inserted into a recess of the fork plate. Then the second motor 21 is energized to ascend the arm 9, and during this ascending movement of the arm, the flange 22a of the probe 22 is engaged with the fork plate 25 and the connection between the nozzle 11 and the probe 22 is broken and the probe descends into the probe supporting member 23. That is to say, the flange 22a of the probe 22 is placed on the flange 23b of the probe supporting member 23. In this manner, the probe 11 can be removed from the nozzle 22. It should be noted that the width of a fork formed in the fork plate 25 is larger than the diameter of the tube-like main body of the probe 22, but is smaller than the diameter of the flange 22a of the probe 22. Then, the first motor 18 is energized again to rotate the arm 9 such that the nozzle 11 is indexed into a-reagent sucking position R above a reagent bottle 8 which contains a reagent to be delivered next. At the same time, the probe removing mechanism is also moved into the relevant reagent bottle 8. In this manner, different kinds of reagents can be successively delivered into the reaction vessels 3 with the aid of the nozzle 11, while it is not necessary to wash the nozzle at time intervals between successive deliveries of reagents, because the nozzle is not brought into contact with reagents. Further since the probes 22 are used exclusively for delivering predetermined reagents, it is also unnecessary to wash the probes.

As shown in FIG. 1 there is further provided a measuring unit 26 along the reaction turntable 2 to measure a test liquid contained in a reaction vessel 3, said test liquid being a mixture of a sample and reagent delivered into the reaction vessel. The measuring unit 26 includes a first portion having a light source and a wavelength selecting filter and a second portion containing a photodetector, said first and second portions being arranged on opposite sides of the reaction vessel, so that the calorimetric measurement can be performed.

FIG. 3 is a schematic plan view showing a second embodiment of the automatic chemical analyzer according to the invention. In the present embodiment, portions similar to those of the first embodiment are denoted by the same reference numerals used in FIGS. 1 and 2. In the present embodiment, a plurality of reagent bottles 8 are arranged on a reagent turntable 31 which is rotatably provided on the base 1. By rotating the reagent turntable 31, it is possible to index any desired reagent bottle 8 into the single reagent sucking position R, and a reagent contained in a reagent bottle indexed into the reagent sucking position R can be delivered into a reaction vessel 3 on the reaction turntable 2 with the aid of the reagent delivery mechanism which is substantially the same as that of the previous embodiment. In the present embodiment, since the reagent is always sucked into a probe 22 at the reagent sucking position R, it is sufficient to provide the probe removing mechanism only at the reagent sucking position R. The remaining construction of the present embodiment is entirely as the first embodiment.

FIG. 4 is a schematic plan view showing a third embodiment of the automatic chemical analyzer according to the invention. Also in the present embodiment portions similar to the previous embodiments are denoted by the same reference numerals used in them. In the third embodiment, there are arranged on the base 1 two reagent turntables 31-1 and 31-2 on opposite sides of the reaction turntable 2 and there are provided two reagent delivering mechanisms 32-1 and 32-2 each of which has the same construction as that illustrated in FIG. 3. On the first reagent turntable 31-1 there are arranged a plurality of different kinds of first reagents, while on the second reagent turntable 31-2 are provided a plurality of different kinds of second reagents. In %,he third embodiment, the delivery of reagents can be effected much more efficiently, so that the analyzing speed can be further improved.

Figure 5:
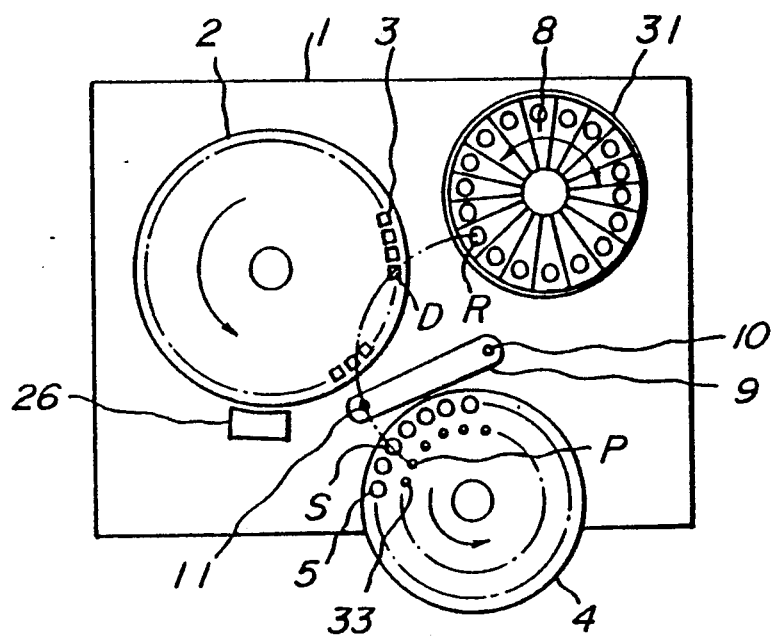
FIG. 5 is a plan view showing a fourth embodiment of the automatic analyzer according to the invention.

FIG. 5 is a schematic plan view depicting a fourth embodiment of the automatic chemical analyzer according to the invention. In the previous embodiments, the sample delivery is effected with the aid of the ordinary liquid delivery mechanism provided separately from the reagent delivery mechanism, but in the present embodiment, the samples and reagents are delivered into reaction vessels by means of a single common delivery nozzle, while the contamination between successive samples, the contamination between successive reagents and also the contamination between samples and reagents can be completely removed. Also in the present embodiment, portions similar to those shown in the previous embodiments are represented by the same reference numerals used in these embodiments. On the base 1 is rotatably arranged the reaction turntable 2 having a plurality of reaction vessels 3 arranged thereon along the periphery of the turntable. The reaction turntable 2 is rotated in the direction shown by an arrow in the step-wise manner. On the base 1 there is further arranged rotatably the sample turntable 4 having a plurality of sample vessels 5 arranged along the periphery thereof. The sample turntable 4 is also rotated intermittently in the direction shown by an arrow. A plurality of reagent bottles 8 containing different kinds of reagents are arranged on the reagent turntable 31 which is provided on the base 1 rotatably in both directions as illustrated by a double headed arrow. On the base 1 there is arranged a single liquid delivery mechanism comprising the arm 9 which is rotated and moved up and down as explained in connection with the first embodiment. The common nozzle 11 is secured to a free end of the arm 9. The arm 9 can be rotated to index the nozzle 11 into a sample sucking position S, a sample probe pick-up position P, a discharging position D and a reagent sucking position R. In the present embodiment, samples contained in the same vessels 5 on the sample turntable 4 are delivered with the aid of sample probes. To this end, a number of sample probes 33 are detachably arranged on the sample turntable 4 in such a manner that each of the sample probes is exclusively used to deliver respective samples. The construction of the reagent delivery mechanism is entirely same as that of the previous embodiments.

Now, the operation of the present embodiment will be explained. At first it is assumed that the arm 9 is in the sample probe pick-up position P. Then the second motor 21 is energized to descend the arm 9 until the tip of nozzle 11 is firmly inserted into the upper mouth of the sample probe 33 set in an opening 4a formed in the sample turntable 4 as shown in FIG. 6. In the present embodiments the sample probe holding member is formed by the opening 4a, but it may be constructed in the same manner as that of the reagent probe holding member. Then the second motor 21 is energized again to lift the arm 9, while the sample probe 33 has been fixed to the tip of nozzle 11. During this ascending movement, a sample probe removing fork plate 34 is driven into such a position that the fork plate is not brought into contact with the sample probe 33. In FIG. 6, the sample probe removing fork plate 34 is arranged movably in the direction perpendicular to the plane of the drawing of FIG. 6.

Next the first motor 18 is driven to rotate the arm 9 until the nozzle 11 is indexed into the sample sucking position S above a sample vessel 5 on the sample turntable 4, and then the second motor 21 is energized again to descend the arm 9 until the sample probe 33 is immersed into a sample contained in the sample vessel 5. By operating the syringe 12, a given amount of the sample is sucked into the sample probe 33. Then the second motor 21 is driven to ascend the arm 9, and the first motor 18 is energized to rotate the arm 9 into the liquid discharging position D above a reaction vessel 3 on the reaction turntable 2. After that the syringe 12 is operated to discharge the sample sucked in the sample probe 33 into the reaction vessel 3. Then, the first motor 18 is energized until the nozzle 11 is indexed into the sample probe pick-up position P above the sample turntable 4, and then the second motor 21 is driven again to descend the arm 9 until the sample probe 33 is inserted into the opening 4a from which the relevant sample probe has been removed. After the sample probe 33 has been fully inserted into the opening 4a, the solenoid of the sample probe removing mechanism is energized to move the fork plate 34 into the moving path of the sample probe 33. Then the second motor 21 is driven to ascend the arm 9. During this upward movement of the arm 9, the flange of the sample probe 33 is engaged with the fork plate 34 and the sample probe is removed from the tip of nozzle 11 and falls into the opening 4a.

Next the first motor 18 is energized to rotate the arm 9 until the nozzle 11 is indexed into the reagent sucking position R above a reagent bottle 8 which contains a reagent to be delivered into the relevant reaction vessel 3. The reagent delivering operation is entirely the same as the previous embodiment, so that the detailed explanation thereof is dispensed with. Briefly explaining, at first the reagent probe 22 contained in the relevant reagent bottle 8 is fixed to the tip of nozzle 11 and a given amount of the reagent is sucked into the reagent probe. Then, the sucked reagent is discharged into the reaction vessel 3, and after that the reagent probe 22 is returned into the reagent probe supporting member 23 provided in the reagent bottle 8. Finally the nozzle 11 is indexed into the sample probe pick-up position P to prepare the delivery of a next sample.

In the manner explained above, in the present embodiment, the single nozzle 11 and single syringe 12 are used to deliver both the sample and reagent, so that the construction of the analyzer can be made much simpler. Further since the sample is delivered with the aid of the sample probe 33 and the reagent is delivered by means of the reagent probe 22, any contamination between the samples, between the reagents, and between the samples and reagents can be effectively removed.

The present invention is not limited to the embodiments explained above, but many alternations and modifications may be conceived by those skilled in the art within the scope of the invention. For instance, in the above embodiments the non-compressed liquid is filled in the nozzle 11, syringe 12 and tube 13, but it is not always necessary to fill the liquid in these portions. Further in the above embodiments, the probe removing mechanism is constructed by the solenoid 24 and fork plate 25, but it may be formed by various devices. Moreover in the first embodiment shown in FIG. 1, a plurality of probe removing mechanisms may be arranged for respective reagent bottles.

As explained above in detail, in the automatic chemical analyzer according to the invention, different kinds of reagents are delivered into the reaction vessels with the aid of the reagent probes each of which is exclusively used to deliver respective reagent, so that contamination between the reagents can be completely avoided without effecting the washing. Therefore, the operating efficiency of the analyzer can be improved to a large extent. Further the analyzer can be made simple in construction, small in size and cheap in cost. Moreover, since the reagent probes are used repeatedly, the running cost can be reduced as compared with the known analyzer using disposable probes.

What is claimed is:

1. An apparatus for delivering a predetermined amount of a liquid comprising:

a container for holding a liquid, said container having an upper wall, a side wall, a bottom wall and an opening formed in said upper wall;

a tubular member inserted into said container through said opening, said tubular member having an upper opening formed at a top thereof and a lower opening formed in a tip thereof, the length of the tubular member being such that the tip of the tubular member is situated slightly above the bottom wall of said container;

a probe having a suction nozzle which is inserted into said tubular member through the upper opening of the tubular member, a tip of the suction nozzle being of such dimension that the tip of the suction nozzle is immersed into the liquid through the lower opening of the tubular member;

a pump connected to said probe for sucking a predetermined amount of the liquid into said probe through said tip of the suction nozzle;

at least one vessel for receiving the liquid sucked into the tip of the suction nozzle of the probe; and driving means for moving said probe relative to said tubular member such that the liquid sucked into the tip of the suction nozzle of the probe is delivered into the vessel.

2. An apparatus according to claim 1, wherein said bottom wall of the container has a depression formed therein at a position which is opposed to the tip of the tubular member.

3. An apparatus according to claim 2, wherein said bottom wall of the container is inclined such that the liquid contained therein is collected into said depression.

4. An apparatus according to claim 1, wherein said driving means comprises a first driving member for moving the probe in an up and down direction, and a second driving member for moving the probe horizontally.

5. An apparatus according to claim 1, wherein said pump consists of a syringe.

* * * * *